United States Patent [19]

Cowley et al.

[11] Patent Number: 5,286,884
[45] Date of Patent: Feb. 15, 1994

[54] THERMOSYPHONIC REACTION OF PROPYLENE WITH TERTIARY BUTYL HYDROPEROXIDE AND REACTOR

[75] Inventors: Roderick S. Cowley, The Hague, Netherlands; Darrell D. Kinzler, Framingham, Mass.

[73] Assignee: Texaco Chemical Company, White Plains, N.Y.

[21] Appl. No.: 918,108

[22] Filed: Jul. 24, 1992

[51] Int. Cl.$^5$ .................. C07D 301/19; C07D 303/04
[52] U.S. Cl. ...................................... 549/529; 422/198
[58] Field of Search .......................................... 549/529

[56] References Cited

U.S. PATENT DOCUMENTS

| 3,849,451 | 11/1974 | Stein et al. | 549/529 |
| 4,847,393 | 7/1989 | Langley | 549/523 |
| 4,891,437 | 1/1990 | Marquis et al. | 549/529 |

FOREIGN PATENT DOCUMENTS 455099 12/1974 U.S.S.R. .............................. 549/529

Primary Examiner—Joseph E. Evans
Attorney, Agent, or Firm—Jack H. Park; Kenneth R. Priem; Carl G. Ries

[57] ABSTRACT

A method and apparatus for continuously catalytically exothermally reacting propylene with tertiary butyl hydroperoxide in a reaction mixture stream comprising a tertiary butyl alcohol solution of catalyst, reacting propylene, reacting tertiary butyl hydroperoxide, propylene oxide and reaction by-products by thermosyphonically circulating the reaction mixture stream around a thermosyphonic reactor loop; continuously removing heat from the circulating stream in a downflow heat exchange zone in the reactor and continuously passing the circulating stream of reaction mixture through an adiabatic zone such as an upflow reaction zone of progressively increasing temperature while withdrawing or displacing a product stream in an amount sufficient to maintain a predetermined volume of reaction mixture in the reactor and whereby the density of the reaction mixture in the heat exchange zone will be greater than the density of the reaction mixture in the adiabatic zone whereby continuous thermosyphonic circulation can be maintained.

10 Claims, 1 Drawing Sheet

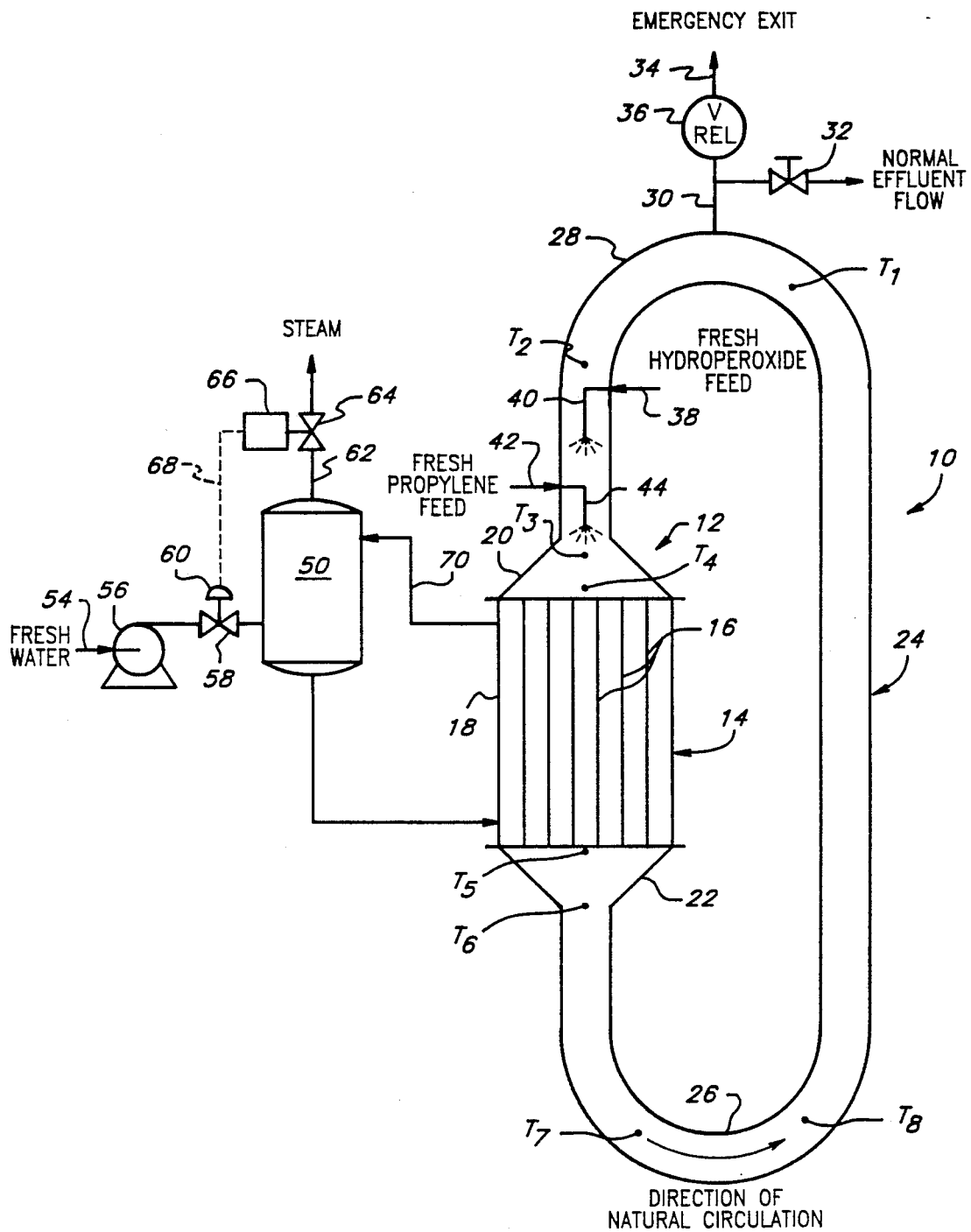

5,286,884

THERMOSYPHONIC REACTION OF PROPYLENE WITH TERTIARY BUTYL HYDROPEROXIDE AND REACTOR

BACKGROUND OF THE INVENTION

1. Technical Field of the Invention

This invention relates to a thermosyphonic method for reacting propylene with tertiary butyl hydroperoxide in solution in tertiary butyl alcohol in the presence of a catalyst to form propylene oxide and additional tertiary butyl alcohol and by-products and to a thermosyphonic reactor useful for the process.

2. Prior Art

It is known to react olefins such as propylene with hydroperoxides such as tertiary butyl hydroperoxide in liquid phase in the presence of a molybdenum catalyst as shown, for example, by Kollar U.S. Pat. No. 3,351,635. See also Kollar U.S. Pat. No. 3,947,500 disclosing the reaction of a hydroperoxide such as, for example, alpha phenyl ethyl hydroperoxide in solution in ethyl benzene with propylene in the presence of a soluble molybdenum naphthenate catalyst.

Marquis et al. U.S. Pat. No. 4,626,596 discloses a method for the preparation of soluble molybdenum/alkylene glycol catalyst and their use in catalyzing the reaction of propylene with tertiary butyl hydroperoxide to provide propylene oxide in additional tertiary butyl alcohol in solution in a solvent such as tertiary butyl alcohol. See also Marquis et al. U.S. Pat. No. 4,650,886.

The reaction is highly exothermic and involves the use of a hydroperoxide which, under adverse conditions is potentially explosive. Therefore, careful control of temperature and the reaction conditions is necessary.

It is also known to conduct gas-liquid chemical reactions in "closed loop" reactors as disclosed, for example, in Papp et al. U.S. Pat. No. 4,312,837 which discloses the use of a closed loop reactor comprising an ascending vertical tube and a descending vertical tube for the reaction of synthesis gas with an olefin in the presence of a catalyst. A reaction of this nature is also known as an Oxo synthesis.

Other references showing closed loop gas-liquid chemical reactors include Westerlund U.S. Pat. No. 3,502,443 which discloses a reactor useful for chlorine dioxide generation, Schuster et al. U.S. Pat. No. 4,482,692 which discloses a gas-liquid reaction conducted in a closed loop such as an oxygenation reaction. Other reactors are shown in Prave et al. U.S. Pat. Nos. 4,545,945 and 4,683,122 wherein a gas and a liquid are brought into contact in a dual zone reactor having an upflow portion and a downflow portion.

Vernon U.S. Pat. No. 3,212,860 discloses a process wherein two immiscible liquid chemicals are reacted in an upstanding reactor having a downflow portion and an upflow portion, such as an alkylation reaction wherein an olefin and isobutane are reacted.

SUMMARY OF THE INVENTION

In accordance with the present invention a closed loop-type reactor is disclosed which is useful for the thermosyphonic liquid phase exothermic reaction of two or more chemicals, such as the liquid phase exothermic reaction of propylene with tertiary butyl hydroperoxide in solution in tertiary butyl alcohol in the presence of a soluble catalyst to provide propylene oxide and additional tertiary butyl alcohol. The reactor comprises an upstanding downflow leg, an upstanding upflow leg, an upper lateral flow line interconnecting the top of the downflow leg with the top of the upflow leg and a lower lateral flow line interconnecting the bottom of the downflow leg with the bottom of the upflow leg, the downflow leg containing an indirect heat exchange segment comprising, for example, a plurality of heat exchange tubes mounted in a shell, the interior of the heat exchange tubes being fluidly interconnected with the downflow leg of the reactor and the shell side of the indirect heat exchanger being fluidly interconnected with a source of a coolant, for example water at its boiling point, which is positioned adjacent to, but above the indirect heat exchange segment and fluidly interconnected with the shell side of the heat exchange segment so that a heat exchange fluid will create a thermosyphonic countercurrent flow through the heat exchange segment shell with or without vaporization and without a need for pumps or other moving parts. One or more inlet lines for providing fresh feed to the thermosyphonic reactor are provided in the downflow leg upstream of the indirect heat exchange segment and an outlet line is provided in the upper lateral leg.

In accordance with the method of the present invention, a propylene feed line and a hydroperoxide feed line are provided in the downflow leg upstream of the indirect heat exchange segment and a discharge line is provided in the upper lateral leg so that a feed solution of tertiary butyl hydroperoxide and catalyst in tertiary butyl alcohol can be charged by the hydroperoxide feed line and so that propylene feed can be charged by the propylene feed line whereby the propylene will mix with the tertiary butyl hydroperoxide in the feed solution to provide a reaction mixture comprising reacting propylene, reacting tertiary butyl hydroperoxide, propylene oxide, tertiary butyl alcohol, catalyst and by-products. The reaction mixture is cooled in the indirect heat exchange segment to provide a lower reaction temperature at the outlet of the heat exchange segment and thereafter, as the reaction mixture flows around the reactor loop the reaction of the propylene with the tertiary butyl hydroperoxide will progressively raise the temperature of the reaction mixture so that the temperature of the reaction mixture in the upflow leg will be greater than the temperature of the reaction mixture in the heat exchange segment. As a consequence, the portion of the reaction mixture in the heat exchange segment will have a greater density than the portion of the reaction mixture in the upflow leg and thermosyphonic flow around the loop will occur without vaporization and also without the need for pumps or other moving parts.

BACKGROUND OF THE INVENTION

In conducting an epoxidation reaction such as one wherein propylene is reacted with tertiary butyl hydroperoxide to provide propylene oxide and additional tertiary butyl alcohol, the catalytic reaction proceeds with the liberation of a significant amount of heat.

Because the chemical reaction takes place only in the liquid phase, it is conventional to provide a continuous stirred reactor such as an autoclave which is provided with a jacket for the circulation of a heat exchange fluid and with a mechanical device such as an impeller for thoroughly stirring the contents of the autoclave. Although this arrangement permits heat recovery from the heat exchange fluid, the process is made more hazardous because it is necessary to provide for seals and flanges such as shaft seals.

In order to improve the safety of the process, to provide for more efficient mixing of the reactants, to provide for efficient recovery of the heat generated by the chemical reaction for use elsewhere in the plant, the process of the present invention is conducted in a closed loop reactor uniquely designed so that there is no need to utilize shaft seals or moving parts or electrically powered equipment which can generate sparks and which relies upon a secure power supply.

BRIEF DESCRIPTION OF THE INVENTION

In its broader aspects, the process of the present invention comprises a method for continuously catalytically exothermally reacting propylene with tertiary butyl hydroperoxide in solution in tertiary butyl alcohol to form propylene oxide and additional tertiary butyl alcohol and by-products by thermosyphonically circulating a reaction mixture stream comprising a tertiary butyl alcohol solution of catalyst, reacting propylene, reacting tertiary butyl hydroperoxide, propylene oxide and reaction by-products around a thermosyphonic reactor; continuously removing heat from the circulating stream in a heat exchange zone in the reactor and continuously passing the circulating stream of reaction mixture through an adiabatic zone such as an upflow reaction zone of progressively increasing temperature while withdrawing or displacing a product stream in an amount sufficient to maintain a predetermined volume of reaction mixture in the reactor and whereby the density of the reaction mixture in the heat exchange zone will be greater than the density of the reaction mixture in the adiabatic zone whereby continuous thermosyphonic circulation can be maintained and continuous mixing with the feed streams with the reaction mixture can be accomplished without the use of externally driven mixers and circulators.

In accordance with another aspect of the present invention a thermosyphonic reactor is provided comprising an upstanding downflow leg, an upstanding upflow leg spaced from the downflow leg, an upper lateral flow line interconnecting the top of the downflow leg with the top of the upflow leg, a lower lateral flow line interconnecting the bottom of the downflow leg with the bottom of the upflow leg, an indirect heat exchange segment being located in the downflow leg and comprising a plurality of heat exchange tubes mounted in a shell, with the interior of the heat exchange tube fluidly interconnected with the downflow leg for the flow of chemical reactants therethrough, means upstream of the heat exchange segment for charging chemical reactants to the thermosyphonic reactor, means in the upper flow line for withdrawing reaction products from the thermosyphonic reactor, a steam release drum located adjacent to and above the indirect heat exchange segment having a charge line interconnecting the bottom portion of the steam release drum with the bottom portion of the shell side of the heat exchange segment, a charge line for delivering water to the steam release drum, a return steam line leading from a point adjacent the top of the shell side of the indirect heat exchange segment to a point adjacent the top of the steam release drum, a steam discharge line mounted adjacent the top of the steam release drum for removing steam therefrom, a pressure control valve mounted in the steam discharge line to control the release of steam therethrough and a flow control valve mounted in the charge line leading to the steam release drum and functionally working with the pressure control valve for regulating the rate at which water is charged to the steam release drum and maintaining thermal equilibrium. The rate at which cooling water is charged to the shell side of the indirect heat exchange segment whereby the rate of cooling of the chemical reactants in the heat exchange segment and hence the temperature at which the chemical reactants flow from the heat exchange segment adjusts itself by thermosyphonic action and generates the steam released through the steam discharge line. Thereby, a temperature differential is automatically maintained between the chemical reactants flowing downwardly through the heat exchange segment and chemical reactants flowing upwardly through the adiabatic reaction segment whereby thermosyphonic flow of the reactants around the thermosyphonic reactor loop is automatically maintained.

In yet another aspect of the present invention, a thermosyphonic reactor is provided comprising an upstanding downflow heat exchange leg and upstanding upflow adiabatic leg laterally spaced from the downflow in the heat exchange leg, an upper lateral line interconnecting the tops of the vertical legs and a lower lateral line interconnecting the bottom of the vertical legs, the downflow leg containing an indirect heat exchange segment having a coolant continuously countercurrently flowing therethrough, a feed line for a tertiary butyl alcohol solution of tertiary butyl hydroperoxide and catalyst and a propylene feed line located upstream of the indirect heat exchange segment and a discharge line located in the upper lateral leg whereby a feed stream composed of a tertiary butyl alcohol solution of a predetermined quantity of tertiary butyl hydroperoxide and catalyst can be charged to the thermosyphonic reactor through the feed line and whereby a predetermined quantity of cool propylene can be charged to the propylene feed line to thereby establish a circulating reaction mixture comprising a tertiary butyl alcohol solution of exothermically reacting tertiary butyl hydroperoxide and propylene, propylene oxide, reaction by-products and catalyst, whereby the cool propylene is brought into direct heat exchange contact with the continuously downward flowing reaction mixture and whereby the reaction mixture is further cooled by indirect heat exchange contact with a coolant such as water in the indirect heat exchange segment to provide a predetermined lower downflow reaction temperature at the exit of the indirect heat exchange segment and whereby the propylene and tertiary butyl hydoperoxide, as they continue to react with each other, will progressively raise the temperature of the reaction mixture as it flows around the loop to thereby maintain a higher temperature in the adiabatic upflow leg whereby a density differential between the portion of the reaction mixture in the upflow leg and the portion of the reaction mixture in the downflow leg will be maintained whereby hydrosyphonic flow will be automatically established.

DESCRIPTION OF THE DRAWING

The drawing is a schematic side elevation view showing, schematically, the manner in which the thermosyphonic reactor of the present invention and the cooling means for the endothermic reactor segment are assembled.

DETAILED DESCRIPTION OF THE PREFERRED EMBODIMENT

Turning now to the drawing, there is schematically shown a preferred embodiment of the thermosyphonic reactor of the present invention designated generally by the numeral 10. The thermosyphonic reactor 10 comprises an upstanding downflow leg designated generally by the number 12 containing an indirect heat exchange segment 14 comprising a plurality of heat exchange tubes 16 in fluid communication with the interior of the downflow leg 12 and a shell 18. Preferably, but not necessarily, the heat exchanger segment 14 and the remainder of the thermosyphonic reactor 12 are of circular cross-section. More preferably, the thermosyphonic reactor 12 is of uniform cross-section except for the heat exchange segment 14 in the downflow reactor and an upper transition segment 20 and a lower transition section 22 fluidly interconnecting the heat exchange tubes 16 of the heat exchange segment 14 with the remainder of the thermosyphonic reactor 10.

The thermosyphonic reactor 10 also comprises an upstanding adiabatic leg 24 which is preferably of tubular uniform cross-section and the bottom of the isothermal downflow leg 12 and the bottom of the adiabatic upflow leg 24 are interconnected in any suitable manner and any suitable means, such as a lateral U-tube 26.

In like manner, the tops of the isothermal downflow leg 20 and adiabatic leg 24 are interconnected by a lateral tube of any desired construction such as an inverted lateral U-tube 28 provided with a discharge line 30 controlled by a valve 32 and provided with an emergency line 34 controlled by a suitable pressure relief mechanism such as a pressure relief valve 36, a rupture disk, etc.

A fresh feed line 38 is also provided in the downflow segment 14 which is preferably provided with downwardly directed nozzle means 40 of any desired construction so that the flow of the fresh feed into the endothermic downflow leg 12 will assist in the circular flow of the reaction mixture about the reaction loop comprising the endothermic downflow leg 12, the interconnecting U-leg 26, the upflow adiabatic leg 24 and the inverted top connecting lateral line 28.

The hydroperoxide feed will normally comprise a tertiary butyl alcohol solution of tertiary butyl hydroperoxide prepared in a downstream unit (not shown) so that the hydroperoxide feed may be at or about the desired reaction temperature to be maintained in the thermosyphonic reactor 12. However, if desired, suitable cooling means (not shown) may be provided for cooling or otherwise adjusting the temperature of the hydroperoxide feed charged to the thermosyphonic reactor 10 by the fresh hydroperoxide feed line 38. A suitable catalyst, such as a molybdenum catalyst is added to the tertiary butyl hydroperoxide feed solution in any desired manner before the solution is charged to the thermosyphonic reactor 10 by feed line 38.

A fresh propylene feed line 42 containing downwardly directed feed inlet nozzle means 44 is also provided. Normally, the propylene will be withdrawn from storage to be charged to the thermosyphonic unit 10 and will therefore be at ambient temperature and can be used as a direct heat exchange fluid.

Suitable means are provided for cooling the reactants in the reaction mixture flowing through the downflow leg 12.

In accordance with the preferred embodiment of the present invention, the reaction mixture flowing downwardly through the downflow leg 12 will be cooled with water, fed to the shell 18 of the heat exchange segment 14 from a suitable storage chamber such as a steam release drum designated generally by the number 50 provided with a water outlet line 52 leading from the bottom of the drum 50 to a point adjacent the bottom of the shell 18.

In accordance with this embodiment, fresh-water is charged to the steam release drum 50 by a fresh water charge line 54 containing a pump 56 and controlled by a valve 58 which is interconnected with a suitable regulating device such as a pneumatic or electrical regulator 60.

An overhead steam withdrawal line 62 controlled by a valve 64, the operation of which is regulated by a pressure sensing control mechanism 66 such as a spring biased or pressure sensitive element or other means.

Within the heat exchange segment 14 the water charged by way of the line 52 is heated by indirect countercurrent contact with the downwardly flowing reaction mixture. It may vaporize and also by thermosyphonic action flow upwardly to an outlet line 70 returning to the steam release drum 50 adjacent the top thereof.

Heated water and steam are returned to the steam release drum 50 by the line 70 leading to the top of the steam release drum 50 so that a wet steam fraction may be discharged overhead by the steam line 62 for use elsewhere in the plant. By regulating the pressure maintained in the steam release drum 50 through appropriate settings of the control members 60 and 66, the rate of withdrawal of steam through the line 66 and the rate at which fresh cooling water is charged by way of the line 54 can be adjusted so that the amount of cooling within the heat exchange segment 14 can be controlled to provide for any desired temperature at the bottom of the heat exchange segment 14 and to maintain a thermal equilibrium in the whole device 10.

PREPARATION OF PROPYLENE OXIDE

In accordance with the present invention, propylene oxide is prepared by reacting propylene with tertiary butyl hydroperoxide in liquid phase in solution of tertiary butyl alcohol in the presence of a catalytically effective amount of a soluble molybdenum catalyst.

Accordingly, the reaction mixture that continuously flows about the elliptical loop defined by the downflow endothermic leg 14, the upflow adiabatic leg 24 and the interconnecting lower and upper legs 26 and 28 will normally comprise a tertiary butyl alcohol solution containing reacting propylene, reacting tertiary butyl hydroperoxide, propylene oxide, tertiary butyl alcohol solvent, catalyst, and reaction by-products.

It is preferable that the reaction mixture contain from about 10 to about 30 wt.% of unreacted tertiary butyl hydroperoxide as the reaction mixture flows around the upper interconnecting leg 28. Accordingly, it is desirable to charge fresh hydroperoxide feed by the fresh hydroperoxide feed line 38, as a tertiary butyl alcohol solution containing from about 30 wt.% to about 80 wt.% of tertiary butyl hydroperoxide and from about 0.1 wt.% to about 0.5 wt.% of a soluble molybdenum catalyst.

Propylene is preferably charged by the fresh propylene feed line 42 at a rate sufficient to provide a charge ratio of about 1 to about 3 moles of charged propylene per mole of charged tertiary butyl hydroperoxide.

The rate of flow of the reactants in the reaction mixture around the elliptical thermosyphonic reactor 10 is preferably regulated to provide a flow rate such that from about 30 to about 50 wt.% of the charged tertiary butyl hydroperoxide is converted to reaction products, principally tertiary butyl alcohol, as it flows around the thermosyphonic reactor 10.

Preferably, the hydroperoxide feedstock charged to the line 38 will contain from about 0.1 wt.% to about 0.5 wt.% of a suitable soluble molybdenum catalyst such as a soluble molybdenum salt of the type disclosed in Kollar U.S. Pat. No. 3,351,635, a molybdenum ethylene glycol complex such as a complex disclosed in Marquis et al. U.S. Pat. No. 4,650,886 and Marquis et al. U.S. Pat. No. 4,654,427, etc.

Desirably, the reaction mixture flowing around the thermosyphonic reactor 10 will contain from about 100 to about 1000 ppm of molybdenum catalyst and more preferably, from about 200 to about 600 ppm, such as, for example, from about 250 to about 500 ppm.

It is preferable that the reaction mixture contain as little water as possible, although a minor amount of water can be tolerated, such as a water level of less than about 0.5 wt.%.

The reaction is preferably conducted at a temperature within the range of about 110° to about 140° C. and the rate of cooling in the reactants in the downflow leg 12 is preferably such that the minimum temperature of the reaction mixture as it exits the heat exchange segment 18 will be from about 5° to about 15° C. lower than the maximum temperature attained in the adiabatic leg 24 and the upper interconnecting leg 28.

Reaction time of the reactants flowing about the endothermic reactor 10 will suitably be from about 5 minutes to about 1 hour.

By way of example, a tertiary butyl hydroperoxide feedstock may be charged by way of the hydroperoxide feed line 38, the feedstock containing about 55 wt.% of tertiary butyl hydroperoxide in solution in tertiary butyl alcohol and about 0.1 wt.% of a soluble molybdenum catalyst. The fresh propylene feed is charged by way of the propylene feed line 42 at a rate such that the mole ratio of charged propylene to charged tertiary butyl hydroperoxide is about 1.6:1. Cooling water is charged by way of the line 52 to the shell side of heat exchange segment 18 in an amount sufficient to maintain the temperature of the reaction mixture as it exits the heat exchange segment 14 at about 117° C. (242° F.), as indicated by the reference numeral $T_6$ in the drawing. Thereafter, the temperature of the reaction mixture will progressively increase due to the exothermic reaction of tertiary butyl hydroperoxide with propylene to a maximum of about 253° F. (123° C.) at a point indicated by the reference numeral $T_2$ in the drawing.

The calculated temperature profile about the thermosyphonic reactor 10 in this specific example at reference points $T_1$ through $T_8$ is given by the following table.

TABLE I

| TEMPERATURE PROFILE | |
| --- | --- |
| Reference Point | Calculated Temperature (°F.) |
| $T_1$ | 251.7 |
| $T_2$ | 253.0 |
| $T_3$ | 241.0 |
| $T_4$ | 241.9 |
| $T_5$ | 241.0 |

TABLE I-continued

| TEMPERATURE PROFILE | |
| --- | --- |
| Reference Point | Calculated Temperature (°F.) |
| $T_6$ | 242.0 |
| $T_7$ | 243.3 |
| $T_8$ | 244.7 |

Since the reaction mixture withdrawn from the thermosyphonic reactor 10 by way of the discharge line 30 will contain unreacted propylene and unreacted tertiary butyl hydroperoxide, the reaction mixture may, if desired, be charged to an appropriate second reactor such as a plug flow reactor (not shown) wherein the reactants continue to react until the reaction is substantially complete.

In accordance with the preferred embodiment of the present invention, the steam release drum 50 is sized so as to contain an inventory of water sufficient to sustain cooling for a predetermined desired period of time in the event that the supply of water to the fresh water feed line 54 should fail for any reason. This time should be sufficient to allow for an orderly reactor shutdown or for the restoration of water from an alternate source. Suitably, the inventory will be such that the water inventory in the steam release drum 50 will provide for at least one hour of cooling without any additional supply of fresh water through the fresh water feed line 54.

As another safety feature, it is to be observed that the the heat balance relied upon for thermosyphonic flow requires the continuous charge of fresh feed through the tertiary butyl hydroperoxide feed line 38 and the propylene feed line 42. If, for any reason, flow of fresh feed through either of the lines 38 or 42 should cease, the amount of cooling achieved in the indirect heat exchange segment 14 can be increased by depressuring the steam drum from a desired operating pressure of from about 5 to about 15 psig. to a lower pressure such as atmospheric pressure (0 psig.).

Having thus described our invention, what is claimed is:

1. A method for continuously catalytically exothermically reacting propylene with tertiary butyl hydroperoxide in solution in tertiary butyl alcohol to form propylene oxide, additional tertiary butyl alcohol and by-products, which comprises:
   a. continuously thermosyphonically circulating a reaction mixture stream comprising a tertiary butyl alcohol solution of catalyst, reacting propylene, reacting tertiary butyl hydroperoxide, propylene oxide and reaction by-products around a thermosyphonic reactor,
   b. continuously removing heat from said circulating stream of reaction mixture in a heat exchange zone in said reactor,
   c. continuously passing said circulating stream of reaction mixture through an adiabatic zone in said reactor to progressively increase the temperature of said circulating stream,
   d. whereby the temperature of the circulating stream will be lower and the density of the circulating stream will be lower in said adiabatic zone than in said heat exchange zone to thereby provide thermosyphonic circulation of said stream,
   e. continuously charging a hydroperoxide feed stream composed of a tertiary butyl alcohol solution containing a predetermined quantity of tertiary butyl hydroperoxide and catalyst and a propylene feed stream to said reactor upstream of said heat exchange zone at predetermined injection rates, and f. continuously withdrawing or displacing a stream of said reaction mixture from said reactor upstream of said hydroperoxide feed stream and said propylene feed stream at a rate sufficient to maintain a predetermined volume of said reaction mixture in said reactor, g. whereby continuous thermosyphonic circulation of said reaction mixture and continuous mixing of said feed streams with said reaction mixture can be accomplished without the use of externally driven mixers and circulators.

2. A method as in claim 1 wherein said hydroperoxide feed stream comprises a tertiary butyl alcohol solution containing about 30 wt.% to about 80 wt.% of tertiary butyl hydroperoxide and about 0.1 wt.% to about 0.5 wt.% of a soluble molybdenum catalyst and wherein the propylene charge stream is charged at a rate sufficient to provide a charge mole ratio of about 1 to about 3 moles of charged propylene per mole of charged tertiary butyl hydroperoxide.

3. A method as in claim 2 wherein the temperature maintained within said reactor is within the range of about 110° to about 140° C. and wherein the maximum temperature in said adiabatic zone is from about 5° C. to about 15° C. higher than the minimum temperature in said heat exchange zone.

4. A method for continuously catalytically exothermically reacting propylene with tertiary butyl hydroperoxide in a reaction mixture comprising a tertiary butyl alcohol solution of reacting tertiary butyl hydroperoxide, reacting propylene, propylene oxide, catalyst, tertiary butyl alcohol and by-products, which comprises:

a. providing a thermosyphonic reactor comprising an upstanding downflow heat exchange leg, an upstanding upflow adiabatic leg laterally spaced from said downflow leg, an upper lateral line interconnecting the tops of said vertical legs and a lower lateral line interconnecting the bottoms of said legs, b. said downflow leg containing an indirect heat exchange segment having a coolant countercurrently flowing therethrough, and also containing a hydroperoxide feed line and a propylene feed line, upstream of said indirect heat exchange segment, said upper lateral leg having a discharge line connected therewith, c. continuously thermosyphonically circulating a stream of said reaction mixture around said thermosyphonic reactor, d. continuously charging a hydroperoxide feed stream composed of a tertiary butyl alcohol solution of a predetermined quantity of tertiary butyl hydroperoxide and catalyst through said hydroperoxide charge line and a predetermined quantity of cool propylene through said propylene feed line for direct heat exchange contact with said continuously downwardly flowing reaction mixture and for indirect heat exchange contact with said coolant in said indirect heat exchange segment to provide a predetermined lower downflow reaction mixture temperature, and e. continuously withdrawing or displacing a stream of said reaction mixture through said discharge line at a rate sufficient to maintain a predetermined volume of said reaction mixture in said reactor, f. whereby propylene and tertiary butyl hydroperoxide contained in said continuously flowing reaction mixture will continuously react with each other as said reaction mixture continuously flows around said reactor and whereby during continuous downward flow of said reaction mixture through said heat exchange portion of said reactor a predetermined lower reaction temperature will be established and whereby the temperature of said reaction mixture will progressively increase as it flows upwardly through said adiabatic portion of said reactor, and g. whereby the density of said reaction mixture will be greater in said heat exchange segment of said thermosyphonic reactor than in the adiabatic segment of said reactor to thereby insure continuous thermosyponic circulation of said reaction mixture around said thermosyphonic reactor.

5. A method as in claim 4 wherein said hydroperoxide feed stream comprises a tertiary butyl alcohol solution containing about 30 wt.% to about 80 wt.% of tertiary butyl hydroperoxide and about 0.1 wt.% to about 0.5 wt.% of a soluble molybdenum catalyst and wherein the propylene charge stream is charged at a rate sufficient to provide a charge mole ratio of about 1 to about 3 moles of charged propylene per mole of charged tertiary butyl hydroperoxide.

6. A method as in claim 5 wherein the temperature maintained within said reactor is within the range of about 110° to about 140° C. and wherein the maximum temperature in said adiabatic zone is from about 5° C. to about 15° C. higher than the minimum temperature in said heat exchange zone.

7. A method for continuously catalytically exothermically reacting propylene with tertiary butyl hydroperoxide in a vertically disposed thermosyphonic elliptical reactor in a reaction mixture comprising a tertiary butyl alcohol solution of reacting tertiary butyl hydroperoxide, reacting propylene, propylene oxide, catalyst and by-products, which comprises:

a. providing said vertically disposed elliptical thermosyphonic reactor with a downflow indirect tubular heat exchange reactor segment located in one leg thereof, said elliptical reactor having a peroxide feed line and a propylene feed line located above said indirect heat exchange segment, and a reactor product outlet line located adjacent to the apex of said thermosyphonic reactor upstream from said inlet lines for withdrawing or displacing a portion of said continuously flowing reaction mixture from said reactor at a rate sufficient to maintain a predetermined volume of reaction mixture in said elliptical reactor, b. continuously charging a feed stream comprising a tertiary butyl alcohol solution containing predetermined quantities of tertiary butyl hydroperoxide and catalyst through said hydroperoxide feed line at a predetermined injection rate and continuously charging a cool propylene feed stream at a predetermined injection rate, c. continuously countercurrently flowing a cooled heat exchange fluid through said heat exchange reactor segment for indirect heat exchange contact with said reaction mixture in an amount and at a rate sufficient to establish a predetermined lower downflow reaction mixture temperature in said heat exchange segment of said reactor, and continuously withdrawing or displacing a stream of said reaction mixture from said thermosyphonic reactor through said outlet line at a rate sufficient to maintain a predetermined volume of said reaction mixture in said elliptical reactor and sufficient to provide for the conversion of about 20% to about 50% of said tertiary butyl hydroperoxide charged to said thermosyphonic reactor, e. whereby propylene and tertiary butyl hydroperoxide contained in said continuously flowing reaction mixture will continuously exothermically react with each other as said reaction mixture continuously thermosyphonically flows around said elliptical reactor and whereby said continuously downwardly flowing reaction mixture will have a predetermined lower reaction temperature as it continuously exits said indirect heat exchange reactor segment and will progressively increase in temperature as it flows upwardly around said elliptical reactor in said adiabatic reactor segment so that the reaction mixture will be at a higher, controlled reaction temperature as it continuously flows upwardly through said other leg of said elliptical reactor, and f. whereby the density of said reaction mixture will be greater in said heat exchange segment of said thermosyphonic reactor than in the adiabatic segment of said thermosyphonic reactor to thereby insure continuous circulation of said reaction mixture around said thermosyphonic reactor.

8. A method as in claim 7:

a. wherein the coolant is water or water and steam, b. wherein a steam release drum is located adjacent and above said indirect heat exchange segment, c. wherein said steam release drum is interconnected with the shell side of said indirect heat exchange means by a water charge line leading from adjacent the bottom of said steam release drum to a point adjacent the bottom of said indirect heat exchange means and by a return line leading from a point adjacent the top of said indirect heat exchange means to a point adjacent the top of said steam release drum, d. whereby water will flow from said steam release drum to the shell side of said indirect heat exchange means for indirect heat exchange contact with said downwardly flowing stream of said reaction mixture, e. whereby said downwardly flowing reaction mixture stream will be cooled and said water will be heated, the rate of flow of said water being such that at least a portion of said cooling water is converted to steam, f. wherein said steam release drum is provided with pressure control means for releasing steam returned to said steam release drum through said return line, and g. wherein said steam release drum is provided with a valve-controlled water charge line for replenishing water removed from said steam release drum as steam.

9. A method as in claim 8 wherein said hydroperoxide feed stream comprises a tertiary butyl alcohol solution containing about 30 wt.% to about 80 wt.% of tertiary butyl hydroperoxide and about 0.1 wt.% to about 0.5 wt.% of a soluble molybdenum catalyst and wherein the propylene charge stream is charged at a rate sufficient to provide a charge mole ratio of about 1 to about 3 moles of propylene per mole of charged tertiary butyl hydroperoxide.

10. A method as in claim 9 wherein the temperature maintained within said reactor is within the range of about 110° to about 140° C. and wherein the maximum temperature in said adiabatic zone is from about 5° C. to about 15° C. higher than the minimum temperature in said heat exchange zone.

* * * * *